United States Patent [19]
Dattagupta et al.

[11] Patent Number: 5,612,200
[45] Date of Patent: Mar. 18, 1997

[54] METHOD AND KIT FOR DESTROYING ABILITY OF NUCLEIC ACID TO BE AMPLIFIED

[75] Inventors: Nanibhushan Dattagupta, San Diego; Thomas B. Ryder, Escondido; Daniel L. Kacian; Keiichi Kamisango, both of San Diego, all of Calif.

[73] Assignee: Gen-Probe Incorporated, San Diego, Calif.

[21] Appl. No.: 218,990

[22] Filed: Mar. 28, 1994

Related U.S. Application Data

[63] Continuation of Ser. No. 903,495, Jun. 24, 1992, abandoned.
[51] Int. Cl.$^6$ .................................................. C12P 19/34
[52] U.S. Cl. .............................. 435/91.2; 935/77; 935/78
[58] Field of Search .............................. 435/91.2, 91.52; 935/77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,786,600 | 11/1988 | Kramer et al. | 435/235 |
| 5,219,727 | 6/1993 | Wang et al. | 435/6 |
| 5,270,183 | 12/1993 | Corbett et al. | 435/91.2 |

FOREIGN PATENT DOCUMENTS

| | | | |
|---|---|---|---|
| 0297379 | 1/1989 | European Pat. Off. | |
| 0320308 | 6/1989 | European Pat. Off. | C12Q 1/68 |
| 9101384 | 2/1991 | WIPO | C12Q 1/68 |
| 9102818 | 3/1991 | WIPO | C12Q 1/68 |

OTHER PUBLICATIONS

Hayatsu et al. Reaction of Sodium Hypochlorite With Nucleic Acids and Their Coustituents, Chem Pharm Bull (1971) 19:2189–2192.

Prat et al. Effet de l'hypochlouite de Sodium Sue les Constituants Pyrimidiques des Bactéries C.R. Acad. Sci. Paris (1965) 260:4859–4861.

Maxam, A.M. and W. Gilbert. Sequencing End–Labeled DNA With Base Specific Chemical·Cleavages, Methods in Enzymology (1980) 65:499–560.

Brunelle, A. and R.F. Schleif. Missing Contact Probing of DNA–Protein Interactions Proc. Natl. Acad. Sci. USA. (Oct. 1987) 84:6673–6676.

Akman, S.A., et al. Base Modification in Plasmid DNA Caused by Potassium Permanganate. Arch. Biochem. Biophys. (Oct.1990) 282:202–205.

Bernofsky, C., et al. Hypochlorite–Modified Adenine Nucleotides: Structure, Spin–Trapping, and . . . Free Radical Research Commun. (1990) 9:303–315, (Abstract).

Albrich, J.M., et al. Biological Reactivity of Hypochlorous Acid: Implications For Microbicidal Mechanisms . . . Proc. Natl. Acad. Sci. USA. (Jan 1981) 78:210–214.

Ou et al., BioTechniques, "Use of UV Irradiation to Reduce False Positivity in Polymerase Chain Reaction", 10:442–445, (1991).

Cimino et al., Nucleic Acid Res., "Post–PCR Sterilization: a method to control carryover contamination for the polymerase chain reation", 19:99–107, (1991).

Longo et al., Gene, "Use of Uracil DNA glycosylase to control carry–over contamination in polymerase chain reaction", 93:125–128, (1990).

Price and Andrus, PCR: How To Kill Unwanted DNA Biotechnology 12: 358 (Mar., 1992).

Barany, Genetic Disease Detection and DNA Amplification Using Cloned Thermostable Ligase. Proc. Natl. Acad. Sci. USA (Jan. 1991) 88:189–193.

*Primary Examiner*—Stephanie W. Zitomer
*Attorney, Agent, or Firm*—Lyon & Lyon

[57] ABSTRACT

Method for destroying the ability of a nucleic acid to be amplified, comprising the step of contacting the nucleic acid with bleach in an amount and for a time sufficient to inhibit the ability of that nucleic acid to be amplified in an amplification reaction.

7 Claims, No Drawings

METHOD AND KIT FOR DESTROYING ABILITY OF NUCLEIC ACID TO BE AMPLIFIED

This application is a continuation of application Ser. No. 07/903,495, filed Jun. 24, 1992, now abandoned.

BACKGROUND OF THE INVENTION

This invention relates to methods for nucleic acid amplification, including the polymerase chain reaction (PCR, U.S. Pat. Nos. 4,683,195 and 4,683,202), the ligase chain reaction (European Patent 320,308) and procedures using RNA polymerase driven amplifications (U.S. Pat. No. 4,786,600 and International Patent PCT/W091/02818).

Diagnosis of human disease has been aided by recent developments in nucleic acid amplification. These methods generate million to billion fold and more copies of a target sequence. Other nonspecific or specific products are also produced, some of which are produced from the primers, e.g., primer dimers in a typical PCR reaction. Such reaction products are potential inhibitors of the desired amplification process. After amplification, the product of the procedure is analysed by hybridization and then discarded. During these processes contamination of laboratory devices, the laboratory bench and other structures may result. This creates a problem in future amplification procedures since the methods are sensitive enough to detect even minute amounts of nucleic acids. In order to solve this type of contamination or cross-contamination problem, several methods have been devised.

For example, a PCR amplified product can be deactivated from further amplification by irradiation with UV light (Ou et al., 10 *BioTechniques* 442, 1991; Cimino et al., 19 *Nucleic Acids Res.* 99, 1991). Such irradiation in the absence or presence of a DNA binding photoactivatable ligand (e.g., isopsoralen) makes the product DNA nonamplifiable but retains the specific hybridization property. In addition, use of a 3'-ribose primer in a PCR reaction produces nucleic acid which can be readily destroyed by alkali. Similarly, other procedures are used to produce specific modified nucleic acids which can be selectively destroyed by treatment with a specific enzyme. Such modified nucleic acids have been produced by amplification in the presence of dUTP as a substrate in a PCR reaction. Deoxy-U containing product DNA can be degraded by a U-specific enzyme making the DNA nonamplifiable (Integrated DNA Technologies Technical Bulletin, Triple C primers 1992; Longo et al., 93 Gene 125, 1990). Many of these methods function well with DNA or its amplified DNA products. These methods, however, require expensive reagents and affect the course of the amplification method, e.g., by requiring longer time and specific conditions.

An object of the present invention is to obviate such problems and to develop simple reagents which are highly efficient in destroying nucleic acids and related amplification products which are potential inhibitors of other amplification reactions.

SUMMARY OF THE INVENTION

The present invention uses chemical agents to destroy nucleic acids, including both RNA and DNA, which are produced by nucleic acid amplification methods. Such RNA and DNA molecules may be of sizes which can be further amplified or which can inhibit an amplification reaction. Such agents include oxidants, reductants and reactive chemicals which modify the primary chemical structure of a nucleic acid. These reagents have the property of making nucleic acids inert towards an amplification reaction, whether the product is RNA or DNA. Examples of such chemical agents include solutions of sodium hypochlorite (bleach), solutions of potassium permanganate, formic acid, hydrazine, dimethyl sulfate and similar compounds.

The present invention features a method of treatment of amplification products or other nucleic acids with the above reagents to destroy the amplification property of such nucleic acids. The method is very simple to use. Treatment of such amplification reaction products with the reagent can be carried out by simple incubation of the products in a test tube, on a membrane, or on a laboratory bench surface with a solution of the chemical agent. The concentration of the reagent and time of incubation can be adjusted depending on the type of surface to be decontaminated, or the expected amount of the products to be destroyed. Incubation temperatures can also be varied as needed. For example, using bleach as the chemical agent, the concentration of bleach can be between 0.1 and 90%, i.e., between about 0.005 and 4.5% sodium hypochlorite. For potassium permanganate treatment, concentrations between 1 mm and 100 mM can be used in an aqueous solution. Formic acid treatment also can be carried out with acid solutions varying in concentrations from a 10 mM to 20M. The times of exposure to the reagent can be as short as a few seconds to overnight. Temperature can be anywhere between 0° and 95° C.

The procedure can be used after any type of amplification noted above. It will function whether the amplification products are RNA or DNA. The procedure can be carried out after performance of the amplification reaction, and analysis of the products. Such analysis can be by hybridization with a specific probe in a homogeneous or heterogeneous format.

DESCRIPTION OF THE PREFERRED EMBODIMENTS

Reagents useful in this invention are generally described above. The invention is further described by the following examples which are not limiting to the invention:

EXAMPLE 1

Bleach

The effectiveness of bleach to destroy amplification products produced by use of two primers and the enzymes reverse transcriptase and T7 RNA polymerase was studied as follows.

In a typical reaction mixture 15 picomoles of primer 1 (which contains one strand of T7 promoter sequence at the 5' end) and 15 picomoles of primer 2 were mixed with an amount of purified RNA target between zero and 50 femtograms. The mixture was placed in a buffer containing Tris/HCl, magnesium and potassium chloride, and solutions of rNTPs and dNTPs (as described by Kacian et al., WO 91/01384, published February 7, 1991, hereby incorporated by reference herein) and heated at 95° C. for 15 minutes and then cooled down to 42° C. Enzymes were added to this mixture and the solution incubated at 37° C. for one hour. The enzyme mixture contained 300 units of MMLV reverse transcriptase and 200 units of T7 RNA polymerase in a buffer solution described by Kacian, supra. After amplification the products were analyzed by hybridization with an acridinium ester labeled probe as described in Kacian, supra. Table 1 shows the chemiluminescence assay results.

TABLE 1

| Amplification results with RNA targets and 270-1 and 270-2 primers | |
|---|---|
| Target (moles × $10^{-21}$) | Relative chemiluminescence (arbitrary units) |
| 3 | 1,649,173 |
| 3 | 1,710,974 |
| 3 | 1,702,449 |
| 0 | 3,952 |
| 0 | 3,575 |
| 0 | 2,646 |

The analysed mixtures included hydrogen peroxide and sodium hydroxide. After analysis, bleach was added such that the final amount in the mixture was between 1 and 80%. The mixtures were incubated at room temperature (about 20° C.) to boiling (about 100° C.) water bath conditions for between a minute and overnight.

An aliquot was taken from the treated mixtures, diluted and added into a second amplification cocktail similar to that described above. The results of such amplification reactions are shown in Table 2. These results indicate the effectiveness of bleach to destroy the nucleic acids present in the mixture.

TABLE 2

| Results of Bleach Treatment | | | | |
|---|---|---|---|---|
| Target added to primary amplification reaction | Target added to secondary amplification reaction | % Bleach | Time (minutes) | RLU (Arbitrary Units) |
| 0 | $3 \times 10^{-21}$ M | 0 | 0 | 1,067 |
| 0 | $3 \times 10^{-21}$ M | 10 | 15 | 1,125,081 |
| $3 \times 10^{-21}$ M | 0 | 0 | 0 | 562,055 |
| $3 \times 10^{-21}$ M | 0 | 10 | 15 | 3,824 |

The results indicate that the time of treatment with bleach can be very short. A 10% final concentration of bleach incubated, 15 minutes at room temperature, was formed adequate to destroy the ability of the nucleic acid to be amplified. Higher concentrations of bleach reduce the time it takes to destroy the products.

It is notable that when no target was present in the first reaction, products inhibitory to amplification in the second reaction were produced. These could be, for example, primer-dimer products. Such inhibitory products are destroyed by bleach (see, line 2 of Table 2).

EXAMPLE 2

Formic acid

An experiment similar to that in Example 1 was performed using 88% formic acid in place of bleach and the results indicate its effectiveness in destroying the ability of the nucleic acid to be amplified.

EXAMPLE 3

Potassium permanganate

An experiment similar to that in Example L was performed with 100 mM potassium permanganate in place of bleach, and the results indicate that it also is effective in this invention.

EXAMPLE 4

Polymerase chain reaction and bleach

A polymerase chain reaction type of amplification was performed with the same set of primers and target as in Example 1 using reverse transcriptase-mediated DNA production from the target RNA. After the amplification, the product was analyzed as described in Example 1 with the minor modification of heating the probe mixture to 95° C. before incubating at hybridization temperature. Bleach treatment was performed in the manner described as in Example 1 with similar results.

Other embodiments are within the following claims.

We claim:

1. A method for inhibiting the ability to be amplified of nucleic acids produced by a previous amplification, comprising the step of:

contacting said nucleic acids produced by a previous amplification with bleach in an amount and for a time sufficient to inhibit the subsequent amplification of said nucleic acids produced by a previous amplification, thereby inhibiting the ability of said nucleic acids produced by a previous amplification to be amplified.

2. The method of claim 1 wherein said bleach is at a concentration between 1% and 50% for a time between 10 seconds and 15 hours at a temperature between 0° C. and 95° C.

3. A kit for inhibiting the ability to be amplified of nucleic acids produced by a previous amplification comprising materials for nucleic acid amplification and bleach.

4. A method for reducing the nucleic acid amplification inhibitory effect of nucleic acids produced by a previous amplification comprising the step of:

contacting said nucleic acids produced by previous amplification method with bleach in an amount and for a time sufficient to reduce the nucleic acid amplification inhibitory effect of said nucleic acids, thereby reducing the nucleic acid amplification inhibitory effect of said nucleic acids produced by a previous amplification on subsequent amplification of nucleic acids.

5. The method of claim 4 wherein said bleach is at a concentration between 1% and 50% for a time between 10 seconds and 15 hours at a temperature between 0° C. and 95° C.

6. The method of any one of claims 1, 2, 4, and 5, wherein said amplification is the polymerase chain reaction.

7. The method of any one of claims 1, 2, 4, and 5, wherein said amplification is polymerase driven amplification.

* * * * *

UNITED STATES PATENT AND TRADEMARK OFFICE
CERTIFICATE OF CORRECTION

PATENT NO. : 5,612,200
DATED : March 18, 1997
INVENTOR(S) : Nanibhushan Dattagupta, et al It is certified that error appears in the above-indentified patent and that said Letters Patent is hereby corrected as shown below:

Column 3, Line 42 : Delete "formed" and insert --found--

Column 4, Line 3: Delete "Example L" and insert --Example 1--

Column 4, Line 40: After "by" insert --a--

Signed and Sealed this

Twenty-third Day of June, 1998

Attest:

BRUCE LEHMAN

*Attesting Officer*  *Commissioner of Patents and Trademarks*